US 8,280,497 B2

(12) United States Patent
Patel

(10) Patent No.: US 8,280,497 B2
(45) Date of Patent: Oct. 2, 2012

(54) IMPEDANCE HYPERAEMIC STRESS ECHOCARDIOGRAPHY

(76) Inventor: Jijibhoy J. Patel, Stockton, CA (US)

( * ) Notice: Subject to any disclaimer, the term of this patent is extended or adjusted under 35 U.S.C. 154(b) by 0 days.

(21) Appl. No.: 12/577,638

(22) Filed: Oct. 12, 2009

(65) Prior Publication Data

US 2011/0087118 A1 Apr. 14, 2011

(51) Int. Cl.
*A61B 5/04* (2006.01)

(52) U.S. Cl. .......................................... 600/509

(58) Field of Classification Search .................. 600/587, 600/509; 601/33, 134, 148, 149, DIG. 20; 606/201, 202
See application file for complete search history.

*Primary Examiner* — Carl H Layno
*Assistant Examiner* — Jeremiah Kimball
(74) *Attorney, Agent, or Firm* — Ray K. Shahani, Esq.; Kin Hung Lai

(57) ABSTRACT

A method for performing echocardiography for use with patient's unable to perform on a treadmill and in which no medications for increasing heart rate are used. Compression cuffs are placed on each of a patient's four extremities and compression is applied rotatingly to subsets of three out of the four cuffs. EKG is monitored before, during, and after application of the sequential decompression, thereby providing an echocardiograph of the patient's heart.

6 Claims, 2 Drawing Sheets

IMPEDANCE HYPERAEMIC STRESS ECHOCARDIOGRAPHY

RELATED APPLICATION(S)

This application is related to U.S. application Ser. No. 12/006,098 filed Dec. 31, 2007 entitled IMPEDANCE HYPERAEMIC STRESS ECHOCARDIOGRAPHY, which is a Non-provisional Application of Provisional Application Ser. No. 60/919,186 filed Oct. 3, 2007, entitled IMPEDANCE HYPERAEMIC STRESS ECHOCARDIOGRAPHY and Provisional Application Ser. No. 60/919,187 filed Oct. 9, 2007, entitled RIGHT VENTRICULAR HAEMODYNAMICS ON BIO Z/IMPEDANCE CARDIOLOGY MACHINE, which is incorporated herein by reference in its entirety, and claims any and all benefits to which it is entitled therefrom.

FIELD OF THE INVENTION

This invention relates to a method of providing a surrogate test for stress echocardiography, and more specifically to such surrogate test to avoid Intravenous (IV) medication and its potentially harmful effects.

BACKGROUND OF THE INVENTION

An echocardiogram, often referred to in the medical community as a cardiac ECHO or simply an ECHO, is essentially a sonogram of the heart. Also known as a cardiac ultrasound, echocardiography uses standard ultrasound techniques to image two-dimensional slices of the heart.

Stress echocardiography is a test that uses ultrasound imaging to determine how the heart muscles respond to stress or increased performance load. The purpose of the procedure is to discover and treat any potential or actual blockage or disease before serious or life-threatening problems develop. Stress echocardiography is different from an exercise stress test in the way that ultrasound images are taken and used for the diagnosis. The test is performed to see whether the heart muscle is getting enough blood flow and, therefore, sufficient oxygen when it is working hard, i.e., under stress. The test will usually be ordered when patients:

- have new symptoms of angina or chest pain;
- have angina that is becoming worse;
- have recently had a heart attack;
- are at high risk for heart disease (before having surgery or when beginning an exercise program); and
- have heart valve problems.

Typically, stress echocardiography includes the following steps:

- the echocardiogram is performed while the patient is rested and inactive;
- the patient is asked to exercise, such as going on a treadmill or given medicine until the target heart rate is achieved in order to reveal how the heart works when the patient is active;
- the blood pressure and heart rhythm (ECG) of the patent is throughout the procedure;
- the ultrasound images are monitored and recorded during the procedure;
- performing a second echocardiogram immediately after the target heart rate has been reached; and
- analyzing ultrasound imaging which will reveal any parts of the heart that may not be receiving enough blood or oxygen because of blocked arteries.

As mentioned earlier, during stress echocardiography the patients are requested to perform exercises such as walking on a treadmill or pedaling on an exercise bike. However, for patients who are not fit enough to perform these types of tasks, they will be receiving a medication such as Dobutamine or other IV drugs to increase their heart rate to the target heart rate before taking the second echocardiogram.

It would be advantageous to avoid the use of any IV drugs on patients who are unable to perform the exercises for a stress echocardiography test. It would be advantageous to provide a surrogate test that could be given to patients for stress echocardiography.

ADVANTAGES AND SUMMARY OF THE INVENTION

The present invention provides an alternative to conventional stress echocardiography in which patients are required to perform certain physical exercises during the test for the purpose of putting their hearts under stress.

One advantage and object of the present invention is to provide an alternative to conventional stress echocardiography such that patients are no longer required to perform acts of physical exercises during the test.

Another advantage and object of the present invention is to provide a safe test in which no IV drugs are required, thus eliminating related side effects.

Yet another advantage and object of the present invention is to provide a surrogate stress test stress to patients who are unable to perform physical exercises.

Yet another and object of the present invention is to provide a less invasive, more cost efficient and convenient alternative to conventional stress echocardiography.

Further details, objects and advantages of the present invention will become apparent through the following descriptions, and will be included and incorporated herein.

DETAILED DESCRIPTION OF THE PREFERRED EMBODIMENT

Figure 1:
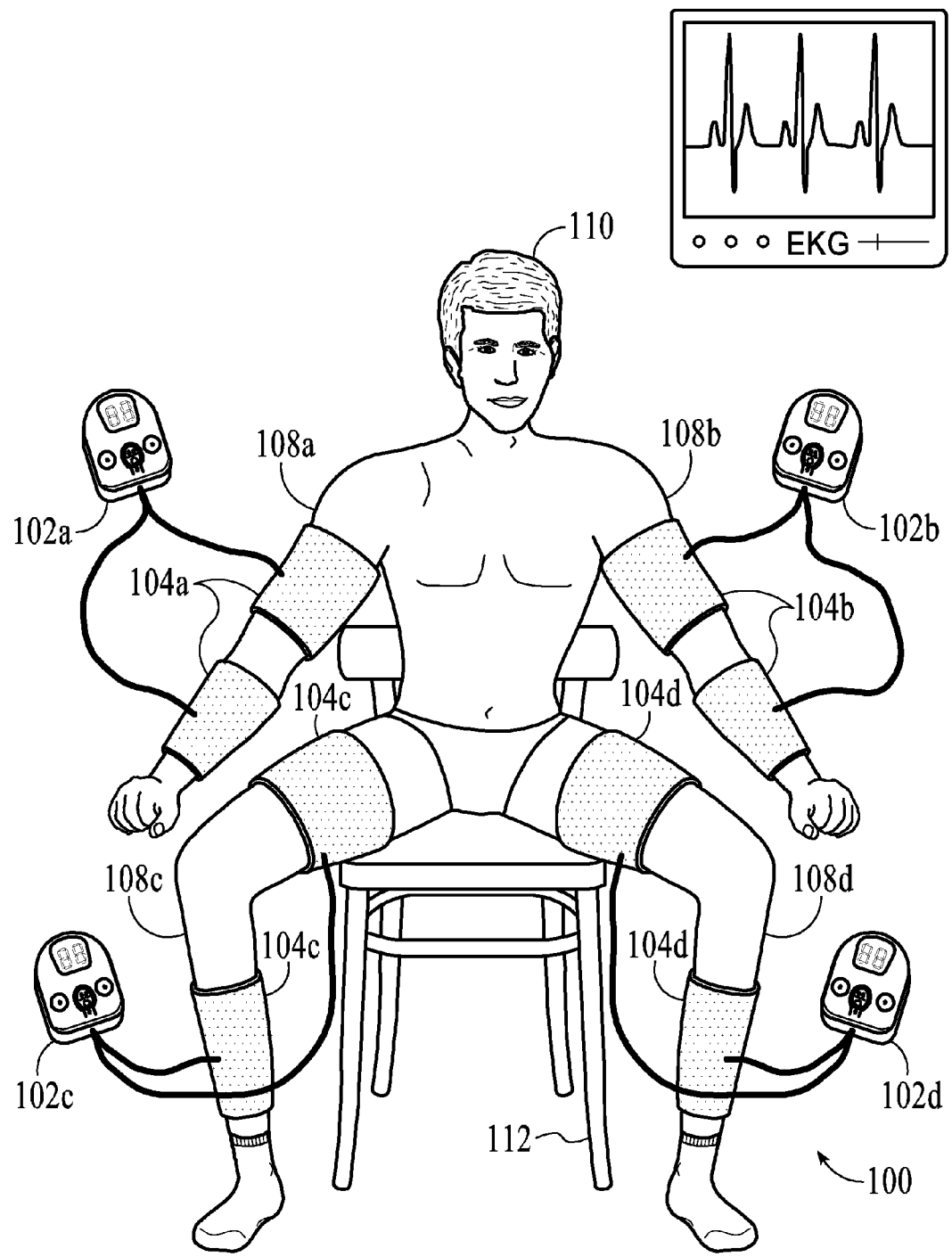
FIG. 1 is a representative drawing showing the method and apparatus 100 of the present invention.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

Surrogate testing involves using a substitute or surrogate material in place of an active pharmaceutical ingredient (API) for verifying the effectiveness of systems for handling these types of potent materials. This allows for in-process testing and manipulation of the systems without having the expense or health concerns of handling the actual API.

Those patients who cannot perform on Treadmill due to orthopedic problems or disability or frailness, or who cannot perform enough to achieve desirable double product. (Systolic B.P.×Heart rate) if 25,000. These patients presently undergo either I.V. Dobutamine. Echo or nuclear stress test with either I.V. Dipyrimadole or I.V. Dobutamine.

Hyperaemic Echocardiography becomes a surrogate test to avoid I.V. medication (the API) and its side effects. The costs and testings that require lots of involvement.

Figure 2:
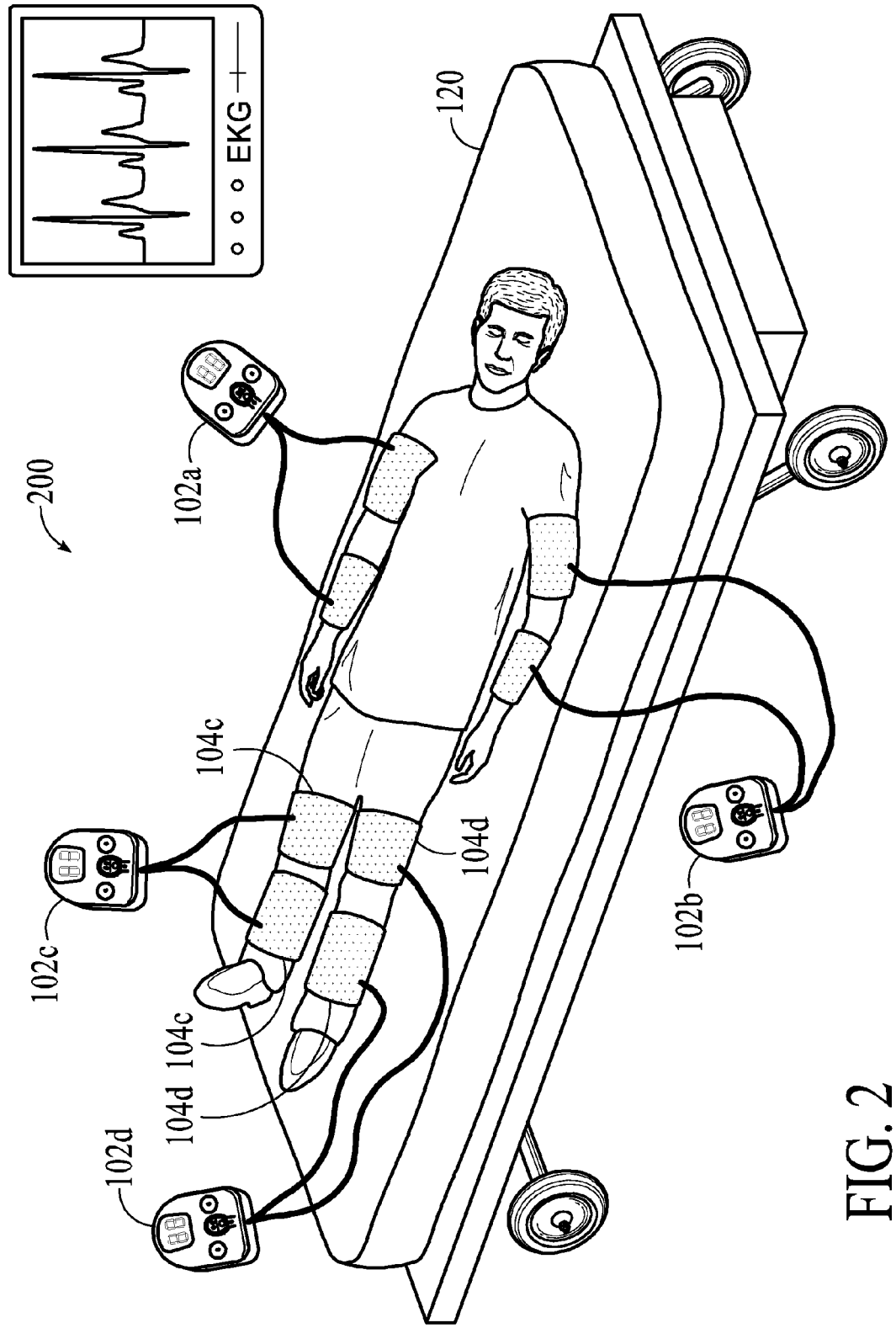
FIG. 2 is another representative drawing showing the method and apparatus 200 of the present invention.

FIG. 1 is a representative drawing showing the method and apparatus 100 of the present invention. FIG. 2 is another representative drawing showing the method and apparatus 200 of the present invention.

Patient 110 undergoing surrogate testing method 100 or 200 can sit on chair 112 or recline on table or bed 120. Compression cuff 104a is placed on the right arm 108a of patient 110. Compression cuff 104b is placed on the left arm 108b of patient 110. Compression cuff 104c is placed on the right leg 108c of patient 110. Compression cuff 104d is placed on the left leg 108d of patient 110. It will be understood that compression cuffs 104a, 104b, 104c and 104d can be one-piece or two-piece, and be fitted over an upper part of the respective extremity 108a, 108b, 108c or 108d, a lower part of the respective extremity 108a, 108b, 108c or 108d, or both the upper and lower parts of the respective 108a, 108b, 108c or 108d.

As indicated, compression cuffs 104a, 104b, 104c and 104d are utilized over all 4 extremities 108a, 108b, 108c and 108d. The rotation can be made by manual or automatic, computer-controlled inflation and deflation utilizing control valved 102a, 102b, 102c and 102d. Initially, any 3 are inflated and one is allowed to deflate, in rotation every 5 minutes, to keep 1 extremity free for the control performed circulation at any one time. A total of 4 cycles are thus performed in approximately 20-25 minutes, thus rotating through all possible combinations of the 3+1 configuration.

Echocardiography is obtained at rest prior to starting initiation and immediately post inflation period when all 4 cycles are completed. The latter serves as hyperemic response to the heart as a "stress" method, without using any I.V. drugs or treadmill exercises as in a conventional stress echocardiography test.

Continuous EKG monitoring is performed during and after the rotation, i.e., complete inflation periods.

When a patient is not able to perform Treadmill stress test for Treadmill with ankle indices for ASPAD diagnosis, then Hyperemic Ankle Indices method is the surrogate for Treadmill with ankle indices, because the deflation of cuff created hyperaernia serves as a treadmill hyperemic response.

This principle is utilized to give a similar hyperemia by cuff method but utilizing all 4 limbs in rotation as described above to render hyperemic stress to the heart.

This study was then compared to the result of stress echocardiography or Nuclear stress where ever it was available to assess its utility as its surrogate test.

It will be noted that in the past, such as pre Furosomide use, a rotating tourniquet was utilized in patients in acute pulmonary edema, to relieve the stress and there were no adverse events for that procedure. Therefore, in the typical patient 110, this rotating cuff method will yield hyperemia should give no adverse events.

Clinical Test Results:

Testing performed on approximately 20 patients resulted in collection of data and analysis of the heart. When compared to stress echocardiography testing, results were similar. Therefore, it is concluded that the surrogate method for EKG monitoring using compression cuffs will provide comparable data to conventional exercise or drug-based echocardiography.

Test Procedure:

Initially, randomly numbered cuffs No. 1, 2 & 3 are inflated for 5 minutes and cuff No. 4 is kept free. Subsequently, cuffs No. 2, 3 and 4 are inflated for 5 minutes and cuff No. 1 is deflated. Thereafter, cuffs No. 3, 4 and 1 are inflated for 5 minutes and cuff No. 2 is deflated. Finally, cuffs No. 4, 1 and 2 are inflated for 5 minutes and cuff No. 3 is deflated.

When all 4 cycles are completed, if more hyperemic responses are required, the same 4 cycles can be repeated.

The boots have B.P. measure and cuffs are inflated to less than systolic pressure, not to cut off the circulation completely. The boots rotation can be made by automatic inflation and deflation utilizing control valved 102a, 102b, 102c and 102d, as it is utilized for external heart compression device that mimics Aortic balloon pump. (counter pulsation).

This simple device then can be utilized as such, without having mammoth cost of aortic balloon counter pulsation device. Therefore this invention will be a surrogate of the conventional exercise stress echocardiography or I.V. Dobutamine stress echocardiography or I.V. Persantine or Dobutamine nuclear stress scan of the prior arts.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

I claim:

1. Rotating compression to a fourth set of three extremities while simultaneously deflating the cuff on the fourth extremity previously under compression, wherein any compression is provided at less than systolic pressure so as not to completely cut off circulation through any given extremity; continuously monitoring the patient's EKG before, during and after the four compression and decompression cycles; and obtaining echocardiography of the patient at rest prior to providing compression to the first set of three of the extremities and immediately post inflation when all 4 cycles are completed, thereby obtaining an echocardiograph of the patient's heart.

2. The method of claim 1, wherein the step of placing compression cuffs on each of a patient's 4 extremities includes the steps of placing compression cuffs on each of the patient's right arm, left arm, right leg and left leg.

3. The method of claim 1, in which compression is provided in 5 minute intervals between rotations.

4. The method of claim 1, in which the rotation of compression is provided by automatic inflation and deflation.

5. The method of claim 4, in which a heart compression device that mimics an aortic balloon pump is utilized to achieve automatic inflation and deflation.

6. A method for performing echocardiography comprising: placing compression cuffs on each of a patient's 4 extremities; applying compression rotatingly to subsets of 3 out of the 4 cuffs, wherein compression is provided at less than systolic pressure so as not to completely cut off circulation through any given extremity; and monitoring the patient's EKG during application of compression rotatingly to subsets of 3 out of the 4 cuffs until at least all 4 cuffs have been rotatingly decompressed, thereby obtaining an echocardiograph of the patient's heart.

* * * * *

UNITED STATES PATENT AND TRADEMARK OFFICE
CERTIFICATE OF CORRECTION

PATENT NO. : 8,280,497 B2
APPLICATION NO. : 12/577638
DATED : October 2, 2012
INVENTOR(S) : Jijibhoy J. Patel Page 1 of 1

It is certified that error appears in the above-identified patent and that said Letters Patent is hereby corrected as shown below:

In the Claims

Column 4, line 48, claim 1 should read:
1. A surrogate method for performing echocardiography for use with patients unable to perform on a treadmill and in which no medications for increasing heart rate are used, the method comprising the following steps:
    Placing compression cuffs on each of a patient's 4 extremities;
    Providing compression on a first set of three of the extremities while simultaneously leaving the cuff on one of the extremities uncompressed;
    Rotating compression to a second set of three extremities while simultaneously deflating the cuff on the fourth extremity previously under compression;
    Rotating compression to a third set of three extremities while simultaneously deflating the cuff on the fourth extremity previously under compression;

Signed and Sealed this
Twentieth Day of May, 2014

Michelle K. Lee
*Deputy Director of the United States Patent and Trademark Office*